US00PP20481P2

(12) United States Plant Patent
Hanes

(10) Patent No.: US PP20,481 P2
(45) Date of Patent: Nov. 17, 2009

(54) ***PELARGONIUM* PLANT NAMED 'AMRI PIKEGS'**

(50) Latin Name: *Pelargonium hortorum*
Varietal Denomination: Amri Pekegs

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/218,882

(22) Filed: Jul. 17, 2008

(51) Int. Cl.
*A01H 5/00* (2006.01)

(52) U.S. Cl. ..... Plt./325

(58) Field of Classification Search ..... Plt./325, Plt./328
See application file for complete search history.

*Primary Examiner*—June Hwu
(74) *Attorney, Agent, or Firm*—S. Matthew Edwards

(57) ABSTRACT

A new *Pelargonium* plant named 'Amri Pikegs,' particularly distinguished by the large flower size, pink flower color with bold red-purple blotch, medium green foliage, good vigor and branching.

1 Drawing Sheet

Latin name of the genus and species of the plant claimed: *Pelargonium hortorum.*

Varietal denomination: 'Amri Pikegs'.

BACKGROUND OF THE NEW PLANT

The present invention comprises a new *Pelargonium,* botanically known as *Pelargonium hortorum,* and hereinafter referred to by the variety name 'Amri Pikegs.'

'Amri Pikegs' is a product of a planned breeding program. The new cultivar 'Amri Pikegs' has a large flower size, pink flower color with bold red-purple blotch, medium green foliage, good vigor and branching.

'Amri Pikegs' originated from a hybridization in a controlled breeding program in Gilroy, Calif. USA. The female parent was an unpatented hybrid seedling identified as '9754-1.' '9754-1' has pink splash color with smaller splash pattern, a darker pink-rose flower color and less vigor than 'Amri Pikegs.'

The male parent of 'Amri Pikegs' was an unpatented hybrid seedling identified as '10071-2.' '10071-2' has white splash color, with smaller flowers, is less floriferous and has a white background flower color compared to 'Amri Pikegs.'

'Amri Pikegs' was selected as one flowering plant within the progeny of the stated cross in 2005 in a controlled environment in Gilroy, Calif. USA.

The first act of asexual reproduction of 'Amri Pikegs' was accomplished when vegetative cuttings were propagated from the initial selection in November 2005 in a controlled environment in Gilroy, Calif. USA.

Horticultural examination of plants grown from cuttings of the plant initiated in November 2005 in Gilroy, Calif. USA, and continuing thereafter, has demonstrated that the combination of characteristics as herein disclosed for 'Amri Pikegs' are firmly fixed and are retained through successive generations of asexual reproduction.

'Amri Pikegs' has not been observed under all possible environmental conditions. The phenotype may vary significantly with variations in environment such as temperature, light intensity and day length.

A Plant Breeder's Rights for this cultivar was applied for in Canada on Dec. 24, 2007. 'Amri Pikegs' has not been made publicly available more than one year prior to the filing of this application.

BRIEF DESCRIPTION OF THE NEW VARIETY

The accompanying photographic drawing shows typical flower and foliage characteristics of 'Amri Pikegs' with colors being as true as possible with an illustration of this type. The photographic drawing shows a flowering potted plants of the new variety and a close-up of the flowers.

DETAILED BOTANICAL DESCRIPTION

The measurements were taken in Salinas, Calif. USA, in July 2008 on plants that were growing in one gallon pots. Culture of these plants started in a greenhouse in February 2008 and were transferred to the outdoors in mid June 2008 under semi-shade. The plants were approximately 4–5 months old.

Color Chart used: The Royal Horticultural Society Colour Chart (R.H.S.) 2001.

BRIEF SUMMARY OF INVENTION

The following observations, measurements, and comparisons describe plants grown outside in Gilroy, Calif., USA. The following traits have been repeatedly observed and are determined to be basic characteristics of the new variety. The combination of these characteristics distinguishes this *Pelargonium* as a new and distinct variety.

TABLE 1

DIFFERENCES BETWEEN THE NEW VARIETY AND A SIMILAR VARIETY

| | 'Amri Pikegs' | 'Fisrix' (U.S. Plant Pat. No. 7,422) |
|---|---|---|
| Foliage color | Medium green | Dark green |
| Flower color | Larger splash/blotch | Smaller splash/blotch |

TABLE 1-continued

| DIFFERENCES BETWEEN THE NEW VARIETY AND A SIMILAR VARIETY | | |
|---|---|---|
| | 'Amri Pikegs' | 'Fisrix' (U.S. Plant Pat. No. 7,422) |
| Plant size | Larger plant habit | Smaller plant habit |
| Pedicel/Peduncle size | Both are shorter | Both are longer |

Plant:

*Form, growth and habit.*—Upright and rounded growth habit. Well-branched.

*Plant height.*—27–30 cm.

*Plant height (inflorescence included).*—33–36 cm.

*Plant width.*—40–48 cm.

Foliage:

*Arrangement.*—Alternate, simple.

*Immature, leaf color, upper surface.*—RHS 137B with a little more yellowish Lower surface: RHS 137B.

*Mature, leaf color, upper surface.*—RHS 137B but a little more yellowish Lower surface: RHS 137B.

*Length.*—5.8–6.4 cm.

*Width.*—9.5–10.5 cm.

*Shape.*—Orbicular.

*Base shape.*—Reniform.

*Apex shape.*—Rounded.

*Margin.*—Medium lobed; irregularly crenate.

*Texture, upper surface.*—Hirsute, glandular hairs.

*Lower surface.*—Hirsute, glandular hairs.

*Color of zone.*—No zone.

*Color of veins, upper surface.*—Indistinct.

*Color of veins, lower surface.*—RHS 138A.

*Petioles color.*—RHS 138A.

*Petioles length.*—6.5–14 cm.

*Diameter of petiole.*—0.3 cm.

*Texture.*—Hirsute; glandular hairs.

Stem:

*Color of stem.*—RHS 144A.

*Length of stem.*—19–23 cm.

*Diameter.*—0.6–0.9 cm.

*Length of internodes.*—2.0–2.5 cm.

*Texture.*—Heavy in glandular hairs; hirsute.

Inflorescence:

*Type.*—An umbel composed of 20 flowers and buds.

*Average number of umbels per plant.*—25.

*Umbel diameter.*—8–10 cm.

*Umbel depth.*—5–5.5 cm.

*Color of peduncle.*—RHS 144A.

*Length of peduncle.*—10–13 cm.

*Peduncle diameter.*—0.4 cm.

*Texture.*—Glandular hairs; hirsute.

*Pedicel color.*—RHS 144A with anthocyanin of RHS 176B.

*Length of pedicel.*—3.0–3.4 cm.

*Diameter of pedicel.*—0.2 cm.

*Texture.*—Glandular hairs; hirsute.

Corolla:

*Form.*—Polypetalous, overlapping.

*Number of petals.*—5.

*Width of flower.*—5.4–5.6 cm.

*Depth of flower.*—1.0–1.5 cm.

*Color upper petals, upper surface.*—Between RHS 73B and RHS 73C ground color; RHS N57A (but more red) blotch with a RHS N57B edge; RHS N57B speckles toward the apex; occasionally an outer margin of RHS 73A; RHS 60C veins.

*Color upper petals, lower surface.*—RHS 73B.

*Length of upper petals.*—3.0–3.1 cm.

*Width of upper petals.*—2.3–2.6 cm.

*Color lower petals, upper surface.*—Between RHS 73B and C ground color; RHS N57A (but more red) blotch with a RHS N57B edge; RHS N57B speckles toward the apex; occasionally an outer margin of RHS 73A.

*Color lower petals, lower surface.*—RHS 73B.

*Length of lower petals.*—2.3–2.8 cm.

*Width of lower petals.*—2.6–2.8 cm.

*Petal shape.*—Obovate.

*Apex shape.*—Rounded.

*Margin.*—Entire.

*Petal texture.*—Papillose.

*Number of petaloids.*—None.

*Duration of flowering.*—Continuous flowering throughout the Summer.

*Lastingness of the flowers.*—About one week.

Bud (when sepals first divide):

*Color.*—RHS 55B.

*Length.*—1.0–1.3 cm.

*Width.*—0.5–0.7 cm.

*Shape.*—Elliptical.

*Number of sepals.*—5, fused at the base.

*Color of sepals.*—RHS 144A.

*Length of sepals.*—0.8–0.9 cm.

*Width of sepals.*—0.3–0.5 cm.

*Sepal shape.*—Linear to lanceolate.

*Apex shape.*—Acute.

*Margins.*—Entire.

*Texture, upper surface.*—Smooth.

*Lower surface.*—Hirsute.

Reproductive organs:

*Pistil.*—1.

*Length.*—1.0–1.2 cm.

*Style color.*—RHS 67A.

*Style length.*—0.4 cm.

*Stigma color.*—RHS 61B.

*Number of anthers.*—6–8.

*Length filaments.*—0.4–0.6 cm.

*Color of filaments.*—RHS N155B but whiter with RHS 67A at the anthers.

*Pollen amount.*—Moderate.

*Color of pollen.*—RHS N25A.

*Fertility/seed set.*—Not observed on this hybrid.

Disease/pest resistance: Disease resistance and/or susceptibility has not been observed on this hybrid.

What is claimed is:

1. A new and distinct variety of *Pelargonium* plant named 'Amri Pikegs,' substantially as illustrated and described herein.

* * * * *

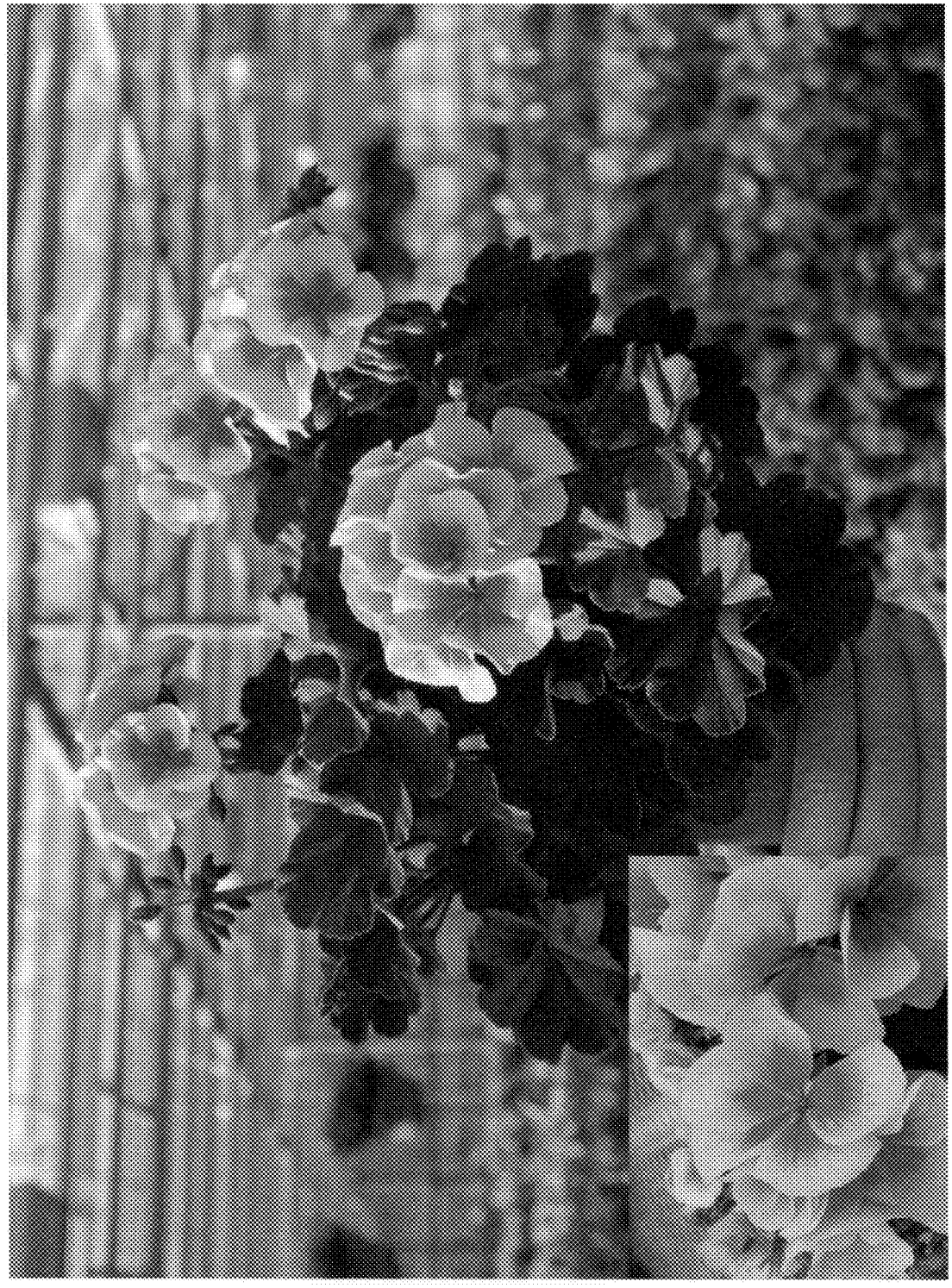

UNITED STATES PATENT AND TRADEMARK OFFICE

CERTIFICATE OF CORRECTION

PATENT NO. : PP 20,481 P2
APPLICATION NO. : 12/218882
DATED : November 17, 2009
INVENTOR(S) : Hanes It is certified that error appears in the above-identified patent and that said Letters Patent is hereby corrected as shown below:

Title page item (50), following "Varietal Denomination:", delete "Amri Pekegs" and insert therefor --Amri Pikegs--

Signed and Sealed this

Twenty-ninth Day of December, 2009

David J. Kappos

David J. Kappos
*Director of the United States Patent and Trademark Office*